(12) United States Patent
Pfister et al.

(10) Patent No.: US 8,059,874 B2
(45) Date of Patent: Nov. 15, 2011

(54) METHOD FOR PRODUCING A THREE-DIMENSIONAL IMAGE DATASET OF A TARGET VOLUME

(75) Inventors: Marcus Pfister, Bubenreuth (DE); Bernhard Sandkamp, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1016 days.

(21) Appl. No.: 11/800,799

(22) Filed: May 7, 2007

(65) Prior Publication Data

US 2007/0258639 A1 Nov. 8, 2007

(30) Foreign Application Priority Data

May 8, 2006 (DE) .......................... 10 2006 021 372

(51) Int. Cl.
*G06K 9/00* (2006.01)
*H05G 1/02* (2006.01)
*G05G 1/60* (2008.04)

(52) U.S. Cl. ............. 382/128; 382/153; 378/8; 378/196

(58) Field of Classification Search .................... 382/128
See application file for complete search history.

(56) References Cited

U.S. PATENT DOCUMENTS

| 5,073,911 | A | * | 12/1991 | Ozaki et al. | 378/17 |
|---|---|---|---|---|---|
| 5,375,156 | A | * | 12/1994 | Kuo-Petravic et al. | 378/9 |
| 5,485,502 | A | * | 1/1996 | Hinton et al. | 378/117 |
| 5,515,416 | A | * | 5/1996 | Siczek et al. | 378/197 |
| 6,120,180 | A | * | 9/2000 | Graumann | 378/206 |
| 6,435,714 | B1 | * | 8/2002 | Bruder | 378/196 |
| 6,459,924 | B1 | * | 10/2002 | Creighton et al. | 600/427 |
| 6,574,297 | B2 | * | 6/2003 | Tam | 378/15 |
| 6,814,490 | B1 | * | 11/2004 | Suhm et al. | 378/198 |
| 7,187,746 | B2 | * | 3/2007 | Sakaguchi et al. | 378/8 |
| 7,257,186 | B2 | * | 8/2007 | Bruder et al. | 378/15 |
| 7,450,682 | B2 | * | 11/2008 | Schonborn et al. | 378/4 |
| 2002/0039403 | A1 | * | 4/2002 | Oota | 378/196 |

OTHER PUBLICATIONS

Siemens Medical Solutions, "AXIOM Adis *d*BA, AXIOM Adis *d*BA DynaCT, Biplane C-arm System with Flat Detector for Angiography", Apr. 1, 2005, pp. 1-24, Data Blatt A91001-M1400-G940-2, Druckzeichen AX CRM NA 04053.

* cited by examiner

*Primary Examiner* — David Zarka

(57) ABSTRACT

The invention relates to a method for producing a three-dimensional image dataset of a target volume by using an examination facility having at least two image recording facilities, each featuring a radiation source and a radiation detector, which can be rotated about an axis of rotation which is arranged perpendicular to the connecting line between the radiation source and the radiation detector, comprising: adjusting the recording areas of the image recording facilities such that the recording areas arranged offset in the z-direction supplement each other to form a recording area, which is enlarged in the z-direction; simultaneously recording two-dimensional images in different orientations by means of the image recording facilities rotating about their axis of rotation; reconstructing a three-dimensional sub-image dataset in each instance from the images of the individual image recording facilities; combining the sub-image datasets to form the three-dimensional image dataset.

15 Claims, 2 Drawing Sheets

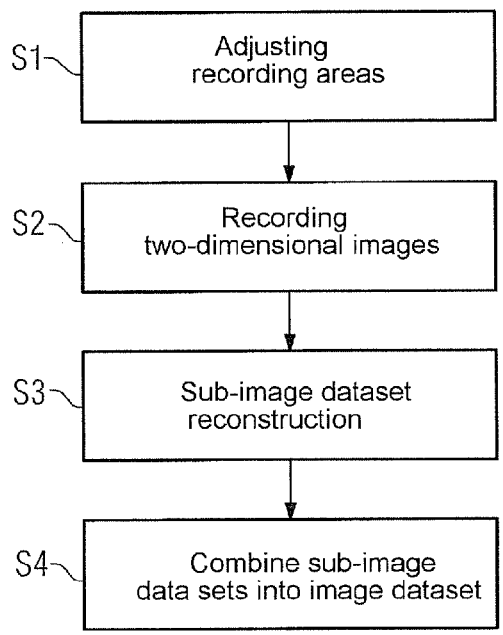
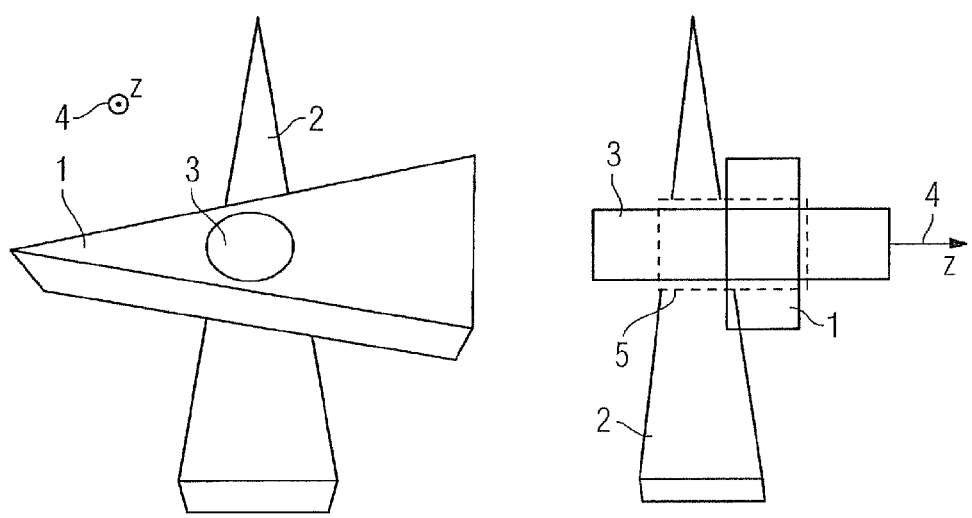

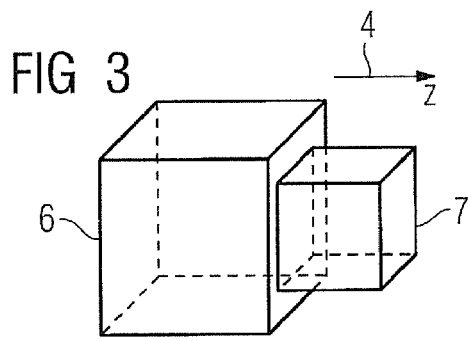
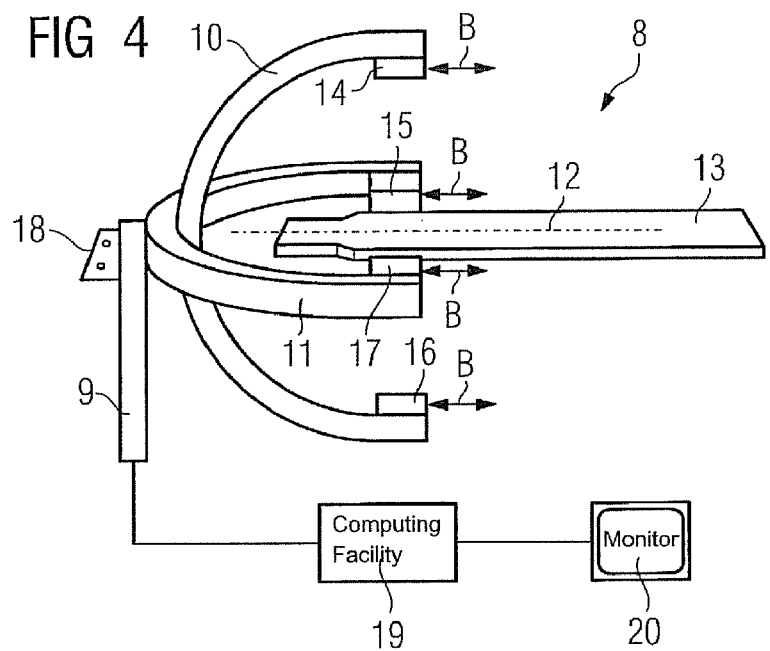
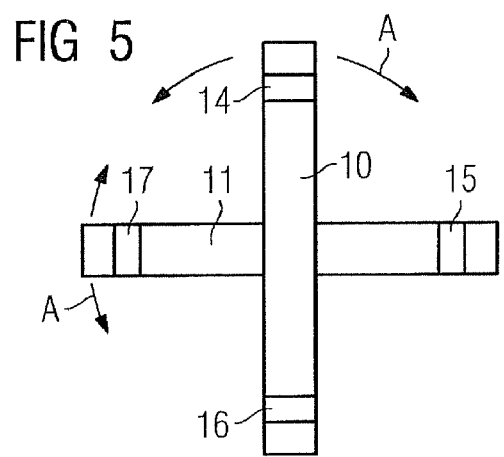

METHOD FOR PRODUCING A THREE-DIMENSIONAL IMAGE DATASET OF A TARGET VOLUME

CROSS REFERENCE TO RELATED APPLICATIONS

This application claims priority of German application No. 10 2006 021 372.6 filed May 8, 2006, which is incorporated by reference herein in its entirety.

FIELD OF THE INVENTION

The invention relates to a method for producing a three-dimensional image dataset of a target volume as well as a medical examination facility which is designed to implement the method.

BACKGROUND OF THE INVENTION

In modern medical examination facilities for recording fluoroscopy images, such as are described for instance from the information in the article "AXIOM Artis dBA/AXIOM Artis dBA DynaCT/Biplane C-arm System with Flat Detector for Angiography" by Siemens Medical Solutions Order No. A91001-M1400-G940-2-7600, publication AX CRM NA 04053, it is not only possible to record two-dimensional fluoroscopy images, but also to obtain three-dimensional image datasets by rotating a C-arm about the patient for instance. In such cases soft parts are typically recorded three-dimensionally and displayed. Three-dimensional angiographs can however also be produced by subtracting contrast agent recordings and native recordings.

The size of the recording area, in other words the radiated region, is determined by the size of the radiation cone, in practice thus by the size of the radiation detector.

For some applications, above all in the abdominal region, but also on limbs such as the legs for instance, larger target volumes, particularly in the longitudinal direction of the patient, the z-direction, must also frequently be covered. To this end, it was proposed to implement two rotations of the C-arm for instance in a consecutive fashion, and to move the patient support by a suitable amount between these recordings. Subsequently three-dimensional reconstruction image datasets are created from each of the two volumes recorded, but the tedious process of registering the images with one another is generally required here in order to allow a joint display. This method proves to be particularly disadvantageous if subtraction images are to be recorded by administering a contrast agent. In this context, it is namely necessary in this instance to administer the contrast agent twice, which may lead to an additional strain being imposed on the patient both in terms of time and also physically.

SUMMARY OF THE INVENTION

The object underlying the invention is thus to specify a method, with the aid of which larger volumes can be recorded in a time-saving manner and without imposing an additional strain on the patient.

To a achieve this object, provision is made for a method for producing a three-dimensional image dataset of a target volume by using an examination facility having at least two image recording facilities, each featuring a radiation source and an x-ray detector, which can be rotated about an axis of rotation which is disposed perpendicular to the connecting line between the radiation source and the radiation detector, comprising the following steps:

Adjusting the recording areas of the image recording facilities such that the recording areas arranged offset in the z-direction supplement each other to form a recording area which is enlarged in the z-direction, Simultaneously recording two-dimensional images in different orientations by means of image recording facilities rotating about their axes of rotation, Reconstructing a three-dimensional sub-image dataset in each instance from the images of the individual image recording facilities, Combining the sub-image datasets to form the three-dimensional image dataset.

The method according to the invention thus takes advantage of the fact that examination facilities are already known in which a number of image recording facilities which can be rotated about an axis of rotation are available. A particular example of this is the so-called biplane facility. In this facility, provision is made for two C-arms which can be rotated independently of one another or coupled thereto, each of which carries an image recording facility having an x-ray source and a radiation detector. In accordance with the invention, the image recording facilities can also be moved in the direction of the z-axis, mostly also the longitudinal direction of the patient. This allows the recording areas of the image recording facilities to be adjusted such that the individual recording areas are arranged offset in the z-direction, so that an enlarged recording area is produced. The individual recording areas can overlap or can adjoin one another. A larger volume can subsequently be recorded than would have been possible with only one of the image recording facilities. This is carried out in the method according to the invention, by rotating the image recording facilities in each instance simultaneously about their axis of rotation and in doing so recording images in different orientations, in other words at different angles. This is carried out simultaneously for the overall recording area which is enlarged in the z-direction, so that a significant time saving is made and the number of times a contrast agent is administered can be reduced.

Three-dimensional sub-image datasets are subsequently reconstructed in each instance from the recording areas of the individual image recording facilities, said sub-image datasets then advantageously having the ability to be combined in a simple manner to form the three-dimensional image data set of the target volume, as a result of the simultaneous recording.

The three-dimensional image dataset can subsequently be displayed in different manners, which can be selected by the user, on a monitor for instance. In such cases both segments through the target volume and also three-dimensional views can be shown. The data of the three-dimensional image dataset can now be processed further, in order to cut out certain areas for instance.

It is not necessary for the image recording areas of all image recording facilities to have the same size. By way of example, in the case of biplane facilities, it is often the case that one image recording facility covers a larger recording area than another. Here too the method according to the invention enables the respective recording areas to be arranged slightly overlapping one another or adjoining one another when offset in the z-direction so that a larger recording area is produced.

In particular, the recording can take place with axes of rotation which are parallel in the z-direction. Some examination facilities are geometrically designed from the outset such that a parallelism of the axes of rotation to the z-direction readily exists. This is nevertheless not imperative for the method according to the invention.

The recording can be carried out in this case with coinciding axes of rotation, it is however also possible, in a particularly advantageous manner, for at least one axis of rotation to be displaced in a direction perpendicular to the z-direction when setting the recording areas. This allows the shape of the enlarged recording area to be ideally adjusted to the gradient of the target volume in the z-direction. If the organ of interest does not run exactly in the z-direction for instance, but is inclined thereto, such a further offset of the axis of rotation enables the gradient of the organ to be remodeled so to speak. This naturally also applies to every other region of interest. It is only necessary to insure in this context that a contiguous enlarged recording area is still produced.

A number of options exist for combining the sub-image datasets to form the three-dimensional image dataset, said options all having the ability to be combined with one another.

By way of example, it is possible to adjust the recording areas such that they overlap in the z-direction. In this context, a rather minimal overlapping, for instance in the range of centimeters, is mostly sufficient. The sub-image datasets can advantageously be combined by registering the overlapping regions of the sub-image datasets. This registration is possible in a particularly simple manner, since the two-dimensional images of the two sub-image datasets were recorded simultaneously, in other words, a registration is still produced in respect of a movement of the patient or the breathing phase of the patient.

The examination facility can be embodied such that the offset of the recording areas in the z-direction and the geometric relationship of the axes of rotation, if necessary the offset of the axes of rotation perpendicular to the z-direction, is known. The examination facility with its image recording facilities is a uniform system, the geometric relationships of which are basically known. If the adjustment facilities for the image recording facilities, for instance C-arms, are designed such that the respective adjustment can be read out, and/or can be detected and can be output, this inevitably reveals how the different recording areas of the individual image recording facilities are arranged in relation to one another. The sub-image datasets can then be combined by allowing for the known offset of the recording areas in the z-direction and if necessary on the basis of the geometric relationship of the axes of rotation, particularly of the known offset of the axis of rotation perpendicular to the z-direction, since it is known where the recording areas lie in relation to one another. In this case, it is possible for both the recording areas to connect directly with one another in the z-direction and also for an overlap to be provided in the z-direction. If the corresponding offsets are not known sufficiently accurately for instance, an additional registration of the overlapping areas of the sub-image datasets allows an improved combination to form a three-dimensional image dataset.

The examination facility can basically naturally also be embodied such that the coordinate systems of all image recording facilities can be easily registered with one another, in other words, such that the examination facility already processes how a corresponding offset has an effect on the registration. In the case of coordinate systems of all image recording facilities which are registered with one another, the sub-image datasets can then be combined with one another by allowing for the registration. On the basis of the known relative position and orientation of the recording areas of the individual image recording facilities to one another, the sub-image datasets can be easily combined to form a three-dimensional image dataset. If necessary, in the case of overlapping recording areas, the overlapping regions of the sub-image datasets can be registered here in addition to monitoring or refining the registration.

Such a registration of the coordinate systems of the individual image recording facilities with one another can in such cases be rigidly predetermined by the geometry of the examination facility or carried out by a calibration on the basis of a phantom. In this context, the phantom is positioned before the target object including the target volume is positioned in the examination facility, said phantom comprising clearly recognizable characteristics on the images, so that the projection matrices between the coordinate systems of the individual image recording facilities can be easily determined.

To achieve a particularly good resolution, provision can be expediently made for the image recording facilities to be pivoted about an angle of 180 degrees plus the aperture angle of the detector when recording the images. Images are then recorded without redundant data in all possible orientations.

The invention also relates to a medical examination facility, in particular a biplane facility, having a computing facility and at least two image recording facilities, each featuring a radiation source and a radiation detector, which can be rotated about an axis of rotation which is disposed perpendicular to the connecting line between the radiation source and the radiation detector, with all axes of rotation in particular being able to be parallel to a z-direction, embodied to implement the method according to the invention. With an examination facility of this type, a fixed offset of the recording areas of the individual image recording facilities can be provided from the outset, with the particular advantage consisting however in designing the image recording facilities offset in respect of one another in the z-direction. An even greater freedom of adjustment can be achieved if there is provision for the axes of rotation is to be displaced perpendicular to the z-direction.

BRIEF DESCRIPTION OF THE DRAWINGS

Further advantages and details of the present invention result from the exemplary embodiments described below as well as with reference to the diagrams, in which;

FIG. 1 shows a flowchart of the method according to the invention,

FIG. 2 shows a schematic diagram of the arrangement of two recording areas in respect of one another, FIG. 3 shows a schematic diagram of the sub-image dataset of two recording areas, FIG. 4 shows a medical examination facility according to the invention, and FIG. 5 shows a view of the C-arms of the examination facility from the z-direction.

DETAILED DESCRIPTION OF THE INVENTION

FIG. 1 shows a flowchart of the method according to the invention. An examination facility is first needed in order to implement the method according to the invention, in this case a biplane x-ray facility having two image recording facilities attached to C-arms which can be rotated about axis of rotation which are parallel in the z-direction independently or coupled thereto. The C-arms or the radiation detectors/radiation sources attached thereto can also be moved in the z-direction.

After a patient has first been positioned on a patient support in the examination facility, the recording areas of the image recording facilities must be adjusted such that the target volume, for instance a leg, is recorded. This is carried out in step S1. The target volume is greater here than any of the recording areas of the two image recording facilities. Within the framework of the method according to the invention, it is now possible to adjust the recording areas of the image recording facilities such that the recording areas arranged offset in the z-direction supplement each other to form a recording area which is enlarged in the z-direction, whereupon the overall target volume can be recognized. A maximum enlarged recording area is achieved if the recording areas adjoin one another in the z-direction. It is however also possible to provide a certain, relatively small overlap, particularly in the range of centimeters, for instance two centimeters, if there is provision for a subsequent registration on the basis of image data or a check is to be carried out by means of a registration of this type.

In step S2, the two-dimensional images are then recorded, from which a three-dimensional image dataset is to be subsequently reconstructed. To this end, the C-arms rotate simultaneously during the recording so that the image recording facilities rotate in a similar manner about their axis of rotation. In this way, two-dimensional images are recorded at regular intervals in different orientations. The number of recorded two-dimensional images and the completeness of the recorded orientations in this case determine the resolution of the three-dimensional image data set achieved. The image recording facilities are advantageously pivoted about an angle of 180. degrees plus the aperture angle of the radiation detector, since then images can be recorded in all conceivable orientations. After the recording, two sets of two-dimensional images are available in each instance to the image recording facilities. These are stored in a computing facility.

Three-dimensional sub-image data sets for the recording areas of each of the image recording facilities are reconstructed in step S3. In such cases, different methods which are known per se can be used for reconstruction. In this case, two sub-image data sets are finally produced which reproduce the respective recording areas of the image recording facility.

These sub-image datasets are now combined in step S4 to form the three-dimensional image dataset of the target volume. To this end, different variants are conceivable, which can also be used in a mutually complementary manner. The examination facility can first be designed such that the displacements of the image recording facilities and/or their axes of rotation, in other words the respective offset, is recorded and is thus known. The respective positions of the recording areas in relation to one another are then also known, so that the sub-image datasets can be combined accordingly. With many such examination facilities, it is however also possible to easily register the coordinate systems of the different image recording facilities with one another. This can either be a fixed registration, which is essentially predetermined, such a registration can however also be achieved by means of calibration. To this end, a phantom is positioned on the patient support for instance, which can then be recorded and the projection matrix which connects the coordinate systems can then be determined on the basis of the characteristic attributes of said phantom. In this case too it is possible in a particularly simple manner to combine the sub-image datasets to form the three-dimensional image data set, which reproduces the enlarged recording area. The method according to the invention can still be used if the offset is not known and no registration of the coordinates system of the image recording facilities is present. The recording areas are then adjusted in step S1 such that a certain overlap, for instance in the range of centimeters, is produced. In a conventional computational registration method, this overlapping area can result in a registration of the sub-image datasets, since it indicates the same area of the target volume in two sub-image datasets, on the basis of which registration the combination to form the three-dimension image data set occurs. All these variants can naturally also be used to supplement each other, start values being able to be predetermined for registration of overlapping regions for example, or a plausibility test can simply be performed. This increases the reliability of the method.

It should be noted here that the simultaneous recording in the z-direction of offset recording areas does not just result in a considerable time saving but also enables in a simpler registration, since for example position changes of the target volume do not play any role.

The three-dimensional image dataset obtained in step S4 can then be displayed and/or processed further in any manner.

FIGS. 2 und 3 now show schematic diagrams of the arrangements of the recording areas relative to one another and/or the resulting sub-image datasets.

FIG. 2 shows the recording areas 1, 2 of two image recording facilities as well as the object 3 to be recorded from two different directions. A corresponding arrow 4 shows the z-direction in each instance. The z-direction visibly corresponds to the longitudinal direction of the object 3, which can be a patient for instance. The tapered recording areas are determined by the path of the radiation from the radiation source to the radiation detector. As can be seen from the drawings, the recording areas 1 and 2 are offset against one another in the z-direction, so that they extend to form a larger recording area 5 in the z-direction, see the sub-image on the right in FIG. 2.

The sub-image datasets resulting herefrom are shown in FIG. 3 in a schematic diagram. The arrow 4 shows in turn the z-direction. The sub-image dataset 6 resulting from the recording area 1 of the first image recording facility is connected in this case in a seamless manner to the sub-image dataset 7 resulting from the recording area 2 of the second image recording facility. The sub-image dataset 7 is in this case somewhat smaller than the sub-image dataset 6, since the recording area 1 is somewhat smaller than the recording area 2. Identically sized recording areas are however also conceivable. In addition, the two-dimensional images have been recorded here with incidental axis of rotation. This is however also not necessary, an offset of the axis of rotation perpendicular to the z-direction is also conceivable. Volumes extending not exactly along the z-direction can also be completely recorded.

FIG. 4 und 5 finally show a medical examination facility 8, with the aid of which the method according to the invention can be implemented with steps S1-S4. The examination facility 8 features two C-arms 10, 11 which can be rotated and are mounted on a support 9, the axis of rotation of said C-arms being parallel in each instance to a z-direction 12, along which the patient support 13 can be moved in each instance. The rotatability of the C-arms 10 is symbolized by the arrows A, see FIG. 5. A radiation source 14, 15 and a radiation detector 16, 17 are arranged in each instance opposite one another on each C-arm. The radiation sources 14, 15, together with the associated radiation detectors 16, 17, each form an image recording facility. The radiation sources 14, 15 and the radiation detectors 16, 17 of each of the two image recording facilities can be moved in each instance in the z-direction when coupled to one another so that the recording areas can be adjusted according to step S1. This offset can be adjusted by way of an operator panel 18. The examination facility 8 however also features a computing facility 19, which is designed to implement the method according to the invention. Furthermore, a monitor 20 is provided.

Provision can additionally be made for the axes of rotation of the C-arms 10, 11 to also be able to be offset perpendicular to the z-direction 12, in order to be able to completely record target volumes which are not completely orientated along the z-direction.

The invention claimed is:

1. A method for generating a three-dimensional image dataset of a patient using an examination system having at least two image recording facilities, comprising:
    moving the image recording facilities in a z-direction by an operator panel;
    mounting the image recording facilities on a support for simultaneously rotating the image recording facilities about axes of rotation;
    recording a plurality of two-dimensional images in a plurality of orientations by the image recording facilities while rotating and moving the image recording facilities;
    reconstructing a plurality of three-dimensional sub-image datasets from the two-dimensional images recorded by the image recording facilities; and
    combining the three-dimensional sub-image datasets with each other to generate the three-dimensional image dataset for an examination of the patient,
    wherein the z-direction is a longitudinal direction of the patient,
    wherein a recording area of the examination system comprises a plurality of recording areas of the image recording facilities, and
    wherein the recording areas of the image recording facilities are offset in the z-direction and supplement each other.

2. The method as claimed in claim 1, wherein the axes of rotation are parallel in the z-direction.

3. The method as claimed in claim 2, wherein the axes of rotation are identical.

4. The method as claimed in claim 1, wherein at least one axis of rotation is perpendicular to the z-direction.

5. The method as claimed in claim 1, wherein the sub-image datasets are combined with each other to generate the three-dimensional image dataset based on a geometric ratio of the axes of rotation.

6. The method as claimed in claim 5, wherein the geometric ratio of the axes of rotation comprises an offset of an axis of rotation that is perpendicular to the z-direction.

7. The method as claimed in claim 1, wherein the sub-image datasets are combined with each other to generate the three-dimensional image dataset based on the offset of the recording areas in the z-direction.

8. The method as claimed in claim 1, wherein the recording areas are overlapped in the z-direction and the sub-image datasets are combined with each other to generate the three-dimensional image dataset by registering the overlapping areas of the sub-image datasets.

9. The method as claimed in claim 1, wherein the recording areas directly connect to each other in the z-direction.

10. The method as claimed in claim 1, wherein coordinate systems of the image recording facilities are registered with one another.

11. The method as claimed in claim 10, wherein the sub-image datasets are combined with each other to generate the three-dimensional image dataset based on the registration.

12. The method as claimed in claim 1, wherein each image recording facility comprises a radiation source and a radiation detector.

13. The method as claimed in claim 12, wherein an axis of rotation of each image recording facility is perpendicular to a connecting line between the radiation source and the radiation detector.

14. The method as claimed in claim 12, wherein each image recording facility is pivoted about an angle of 180 degrees plus an aperture angle of the radiation detector.

15. A medical examination system for generating a three-dimensional image dataset of a patient, comprising:
    an image recording facility comprising a radiation source and a radiation detector that is rotated about an axis of rotation perpendicular to a connecting line between the radiation source and the radiation detector;
    a further image recording facility comprising a further radiation source and a further radiation detector that is rotated about a further axis of rotation perpendicular to a further connecting line between the further radiation source and the further radiation detector;
    an operator panel that moves the image recording facility and the further imaging recording facility in a z-direction;
    a support that mounts both the image recording facility and the further image recording facility for simultaneously rotating the image recording facility and the further imaging recording facility about the axis of rotation and the further axis of rotation to record a plurality of two-dimensional images of the patient in a plurality of orientations; and
    a computing facility that:
        reconstructs a plurality of three-dimensional sub-image datasets from the images recorded by the image recording facility and the further imaging recording facility, and
        combines the three-dimensional sub-image datasets with each other to generate the three-dimensional image dataset,
    wherein the z-direction is a longitudinal direction of the patient,
    wherein a recording area of the examination system comprises a plurality of recording areas of the image recording facilities, and
    wherein the recording areas of the image recording facilities are offset in the z-direction and supplement each other.

* * * * *